United States Patent [19]

Miller

[11] 4,079,737
[45] Mar. 21, 1978

[54] CONTROL VALVE FOR INFUSION SYSTEM
[75] Inventor: John J. Miller, Marietta, Ohio
[73] Assignee: Med-Pak Corporation, Charleston, W. Va.
[21] Appl. No.: 712,212
[22] Filed: Aug. 6, 1976

Related U.S. Application Data

[63] Continuation-in-part of Ser. No. 541,053, Jan. 14, 1975, abandoned.

[51] Int. Cl.² .............................................. A61M 5/14
[52] U.S. Cl. ................................ 128/214 R; 128/274; 251/207
[58] Field of Search ........... 128/214 R, 214 B, 214 C, 128/214 E, 214 F, 214.2, 227, 274; 251/207, 209

[56] References Cited
U.S. PATENT DOCUMENTS

| | | | |
|---|---|---|---|
| 3,276,472 | 10/1966 | Jinkins et al. | 128/214 R X |
| 3,785,378 | 1/1974 | Stewart | 128/214 C |
| 3,851,668 | 12/1974 | Benjamin | 128/214 C |
| 3,868,973 | 3/1975 | Bierman et al. | 128/214 R X |
| 3,877,428 | 4/1975 | Seagle et al. | 128/214 R |
| 3,880,401 | 4/1975 | Wiltse | 128/214 R |

Primary Examiner—Dalton L. Truluck
Attorney, Agent, or Firm—Cennamo, Kremblas & Foster

[57] ABSTRACT

Apparatus for use in hospitals and the like for administering to a patient medicated liquid solutions, or blood. The improvement comprises an improved control valve for regulating and filtering the fluid flow of said solutions into the body. The liquid control valve is of a vernier control type with a selective adjustment to the prescribed rate of fluid flow with limit stops for positive shut-off, and full by-pass. The valve is positioned on the patient adjacent the point of entry of the fluid into the body. The apparatus — adaptable to the commercial infusion administration single use disposable kits — comprises a tapered fluid control spool, having a series of longitudinal grooves. With the spool resiliently snapped into and positioned in a housing the grooves are graduated openings that traverse the fluid supply port. The length, depth, shape and spacing of the grooves together with geometric shape of the supply port provides a variable resistance to the fluid flow to provide an exact program of flow. The spool housing valve further includes in combination therewith a filter. The outside configuration of the control valve is adapted to be secured to the wrist, ankle, or body of the patient in a manner that is safe from accidental operation.

13 Claims, 7 Drawing Figures

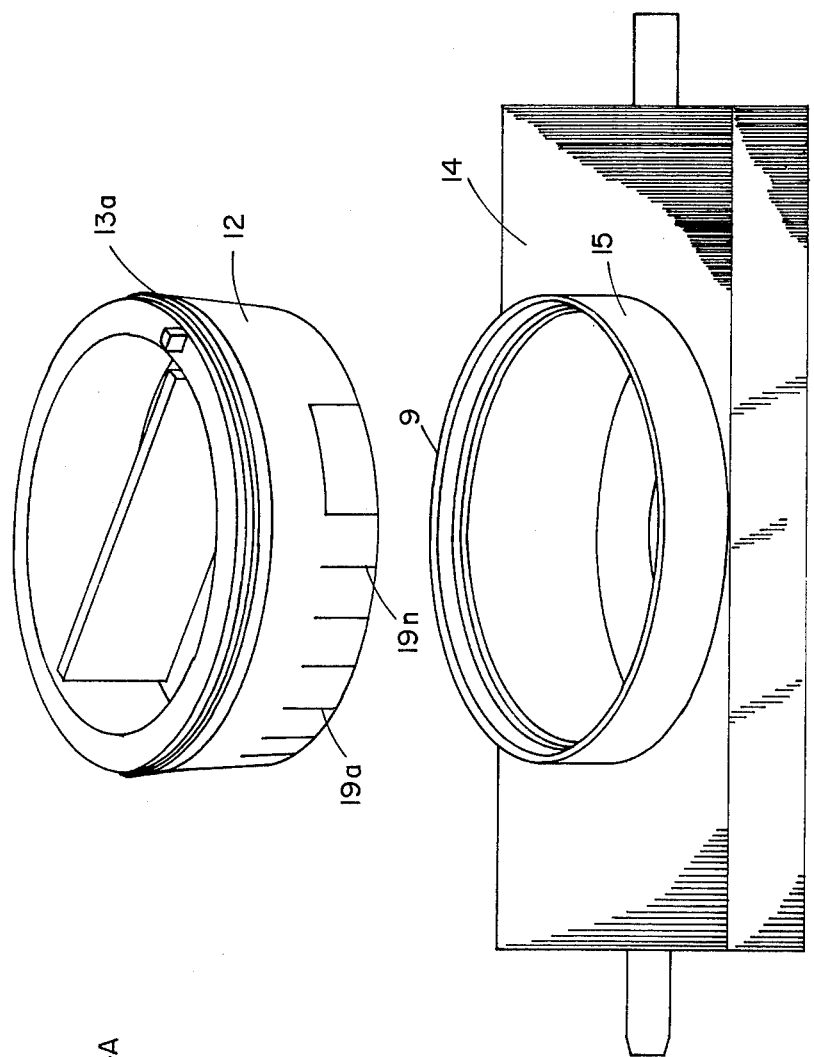
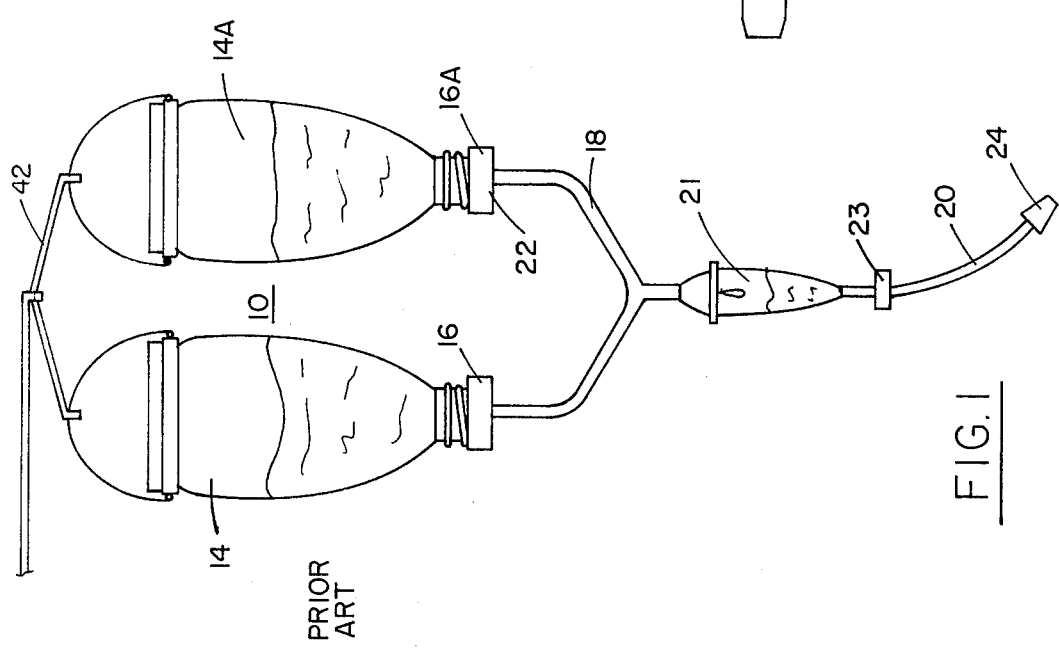
FIG.3
FIG.1 PRIOR ART

CONTROL VALVE FOR INFUSION SYSTEM

This application is a continuation-in-part of Ser. No. 541,053, filed Jan. 14, 1975 now abandoned.

BACKGROUND

Liquids are administered in hospitals to patients for many purposes — the most common perhaps being the intravenous fluid infusion. These infusion kits are disposable, one time use adminstration sets and generally include an inverted glass bottle filled with sterilized liquid solutions such as salt, mineral, sugar, electrolytes, and anticiotics. The solution is drained from a bottle through the flexible tube for infusion into the patient through a needle in the patient's vein. Commercial apparatus on the market include disposable kits that comprise a plastic tubing with a means at one end for entering the bottle to drain the fluid and an air inlet to replace the fluid as it is drained. At the other end ot the tube means are provided to connect with an injection needle. Other bottles in use are of the collapsible type and hence do not require the replacement of air.

PRIOR ART

Present infusion apparatus in commercial use includes the human element of the operator in the control of fluid flow into the patient. The doctor prescribes the volume of solution which is to be administered evenly over a period of time. The attendant operator calculates a flow-rate (millileters per hour) which fulfills the prescription. The flow rate then is converted to drops-per-minute through a second calculation using a conversion factor which matches the drip-chamber installed in the apparatus.

The operator sets-up the prescribed flow rate by mentally counting the number of drops falling into the drip chamber over a timed interval which is usually measured in seconds. The operator then manipulates a flow control to establish the computed drop rate. The control device is commonly a roller clamp or threaded clamp device that regulates flow by pinching the tubing from which liquid flows from the bottle drip chamber to the injection needle or catheter. This procedure for establishing the prescribed flow rate is necessarily exacting and time consuming.

The control devices are unstable since the pinching of the plastic tube creates a highly concentrated load in the areas contacted by the clamp. This load creates a contact stress and the plastic material yields into a cold flow state to reduce the stress. This yielding occurs over a period of tube and results in a continuous change in geometry of the tube, causing further restriction in flow and a decreasing flow rate. The reduction in the flow rate is not readily apparent to the operator since he must recalculate the drip rate to determine the change. The same cycle begins again after the operator again completes the time consuming procedure of setting the prescribed rate.

Further, the roller clamp control devices are unsafe. The roller is held in position by the squeeze force of the tubing. This force reduces as the tubing yields and the roller is free to slip along its inclined plane ramp to a more open position. This greatly increases the flow rate and produces an uncontrolled or "run-away" condition which can cause death to the patient under certain conditions.

The flow rate also tends to decrease due to changes in the height of fluid in the supply bottle. It is common practice to slide the control along the tubing to a position immediately below the drip chamber. In this position the inlet pressure at the clamp control (fluid column height x density) can vary up to 50%, causing an approximate 50% decrease in flow rate.

In addition, the controls which operate by pinching the tube have very high-gain flow rates due to the small diameter of the tubing. A small movement in the roller produces a large change in flow. High gain systems are necessarily difficult to adjust to a prescribed flow position.

CROSS REFERENCE

Reference in made to my co-pending patent application, Ser. No. 339,839, filed Mar. 3, 1973 now U.S. Patent No. 3,939,832 for Liquid Flow Regulator and Monitor Infusion System. There is disclosed therein an infusion control system that is located at or immediately adjacent to the entry point to the patient's body. The entry point may be either at the needle — or as in certain instances — to a catheter.

The control valve has a positive on/off and intermediate flow rate. It does not pinch, crimp, or impede the liquid flow through the tubing. Further, the fixed position of the control adjacent to the body entry point provides a significant reduction in control inlet pressure; 2½ times less than present control valves which are commonly positioned on the tubing near the supply bottle.

SUMMARY OF THE INVENTION

The present invention in its preferred embodiment is an improved control valve and apparatus to be utilized as shown in the aforementioned co-pending patent application. The improved valve is substituted for that shown therein.

The control valve of the present invention comprises generally a rectangular housing having an inlet opening and an outlet opening. A spool co-axially rotatable within the housing controls the amount of fluid that passes from the inlet opening to the outlet opening. The spool comprises a series of equally spaced longitudinal grooves in its outer periphery. The length, shape, depth, and spacing of the grooves co-act with the inlet port geometry to control the rate of liquid flow. The apparatus provides vernier-type of liquid flow control with limit stops for positive off, and fully by-pass flow. The coacting tapered surfaces of the spool and the housing are such that there will always be a non-impeded action, that is, prevents galling yet contacts sufficiently to act as a seal. The spool is resiliently snapped into position and retained in the housing. The control valve is positioned at the end of the tubing at the point of entry into the body to provide a lower change in inlet pressure over those controls positioned intermediate on the tubing. There is further incorporated in the control valve per se a filter positioned in the fluid path between the spool and housing that is operative to eliminate a substantial amount of germs as well as decontaminate, particulate, etc.

OBJECTS

It is accordingly a principal object of the present invention to provide a new and improved reliable apparatus for controlling over a full range the infusion of liquid into the body of the patient.

A further object of the invention is to provide such apparatus that is compatible without change in the commercial apparatus for the infusion of liquids presently marketed.

Another object of the invention is to measureably control with a predetermined flow program the fluids infused into the body with a finite control but yet without the attended disadvantages noted in the prior art.

Another object of the present invention is to provide such a control valve that further includes a filter.

Still another object of the present invention is to provide such a control that provides a reduction in operator maintenance time, an easier off-reset operation, and a low manufacturing cost but yet having a reproducible flow program.

Other objects and features of the present invention will become apparent from the following detailed description when taken in conjunction with the drawings in which:

BRIEF DESCRIPTION OF DRAWINGS

FIG. 1 is an overall illustration of prior art apparatus of gravitational flow type for the infusion of liquids into the body.

FIG. 3 is an exploded view in perspective of the preferred embodiment shown in FIG. 2.

DESCRIPTION OF THE PREFERRED EMBODIMENTS

Figure 2:
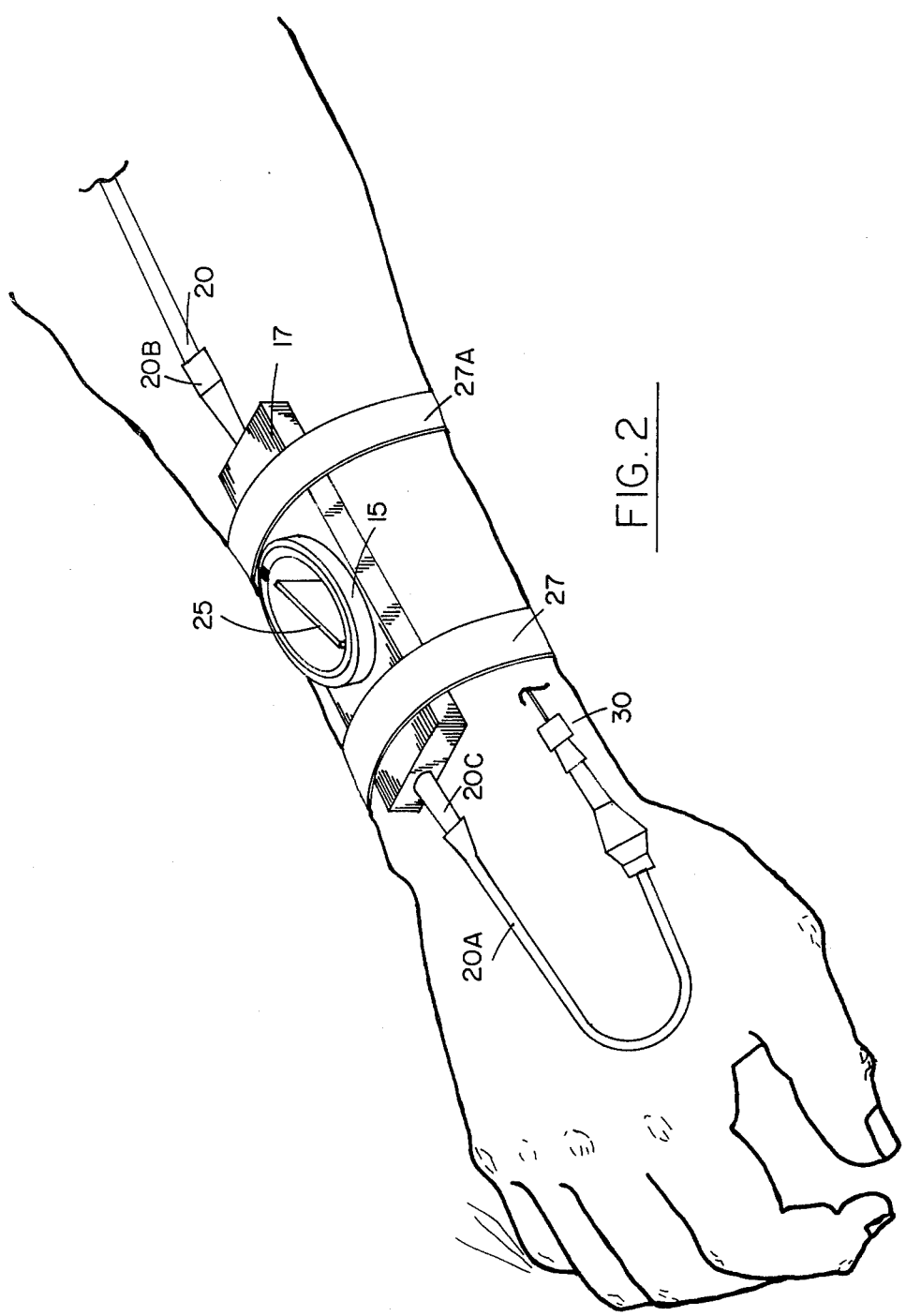
FIG. 2 is an overall view in perspective of the preferred embodiment as adaptable to the arm of a patient.

With particular reference to FIG. 1, a pair of conventional intravenous bottles or liquid containers 10 are supported in the conventional manner by an upstanding support pedestal 42. The bottles 10 are filled with a sterilized liquid solution 14 and 14a that is intended to be infused into a patient. For instance, the solution 14 may comprise a sugar, salt or mineral solution, and the solution 14a may comprise electrolytes or antibiotics. Alternatively, blood may be metered from the bottle 10 into a patient or again the liquid may be an anesthetic.

The stoppers 16 and 16a are connected to the bottles 10 and includes a spikes for piercing the seal on the ends of the bottles. The spike includes an outlet aperture to allow the solution 14 to flow from bottle 10 to the tubing 18. The liquid solutions 14 and 14a fall into a drip chamber 21 and flow down the flexible plastic tube 20 for infusion into the patient. Generally, the end of tube 20 is connected to a needle or catheter inserted into the patient.

Stopper 16 includes an air inlet 22 also extending into the inverted bottle for venting of air or other gas into the bottle 10. The venting of air is to enable the replacement of the liquid solution 14 flowing from the bottle 10 with air for proper operation of the infusion system. An unimpeded air inlet is desired to enable the venting of air into the bottle. Air venting is not needed if a plastic collapsible bag is used in lieu of the bottle 10. Since the bottle 10, caps 16, the Y tubing 18, drip chamber 21 and flexible tube 20 are all conventional and are widely used throughout hospitals, further detail description is not necessary. Also normally included with the commercial IV sets is a flow control mechanism 23 either of the threaded clamp or the roller clamp type.

In accordance with the general concepts of the invention a new and improved control valve as shown in FIG. 2 is strapped to the arm of the patient. The end of the tubing 20 is fitted into the input side. A needle, catheter, needle set, or parenteral set is fitted into the output side. The overall system remains air tight and sterile.

Particularly the end of the tubing 20 is normally fitted with a luer type adaptor 20b. This adaptor has fitted thereon an injection needle or catheter to be inserted into the body of the patient. The apparatus of the present invention utilizes the adaptor 20b as the input to the central valve 17. An extension 20c has fitted thereon a very short section of tubing 20a. In this way the control valve 17 is intermediate the output end 20b and the input end of the injection needle 30.

It is to be noted that adjustment knob 25 is a pointer bar recessed within the outer housing 15. This makes adjustment deliberate hence reducing accidental or inadvertent tampering. As will be pointed out below the matched fitting of knob 25 and housing 15 eliminates any slippage.

Housing 15 is secured to the patient's arm or leg with straps or tape 27 and 27a. This permits one hand operation of the adjustment knob 25 and relieves strain due to the weight of the tube 20 from moving the needle 30.

Figure 4:
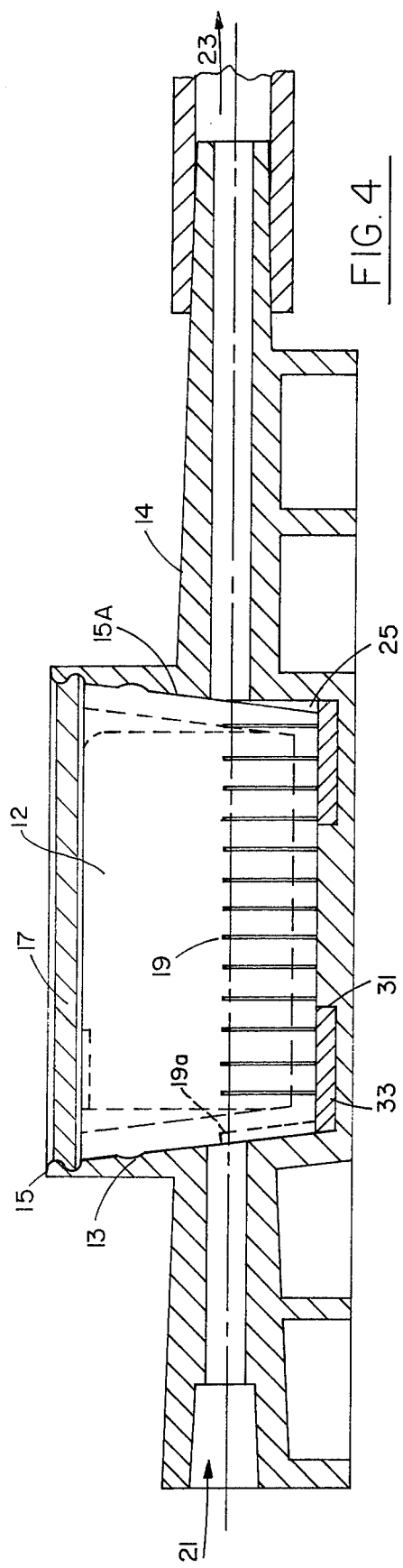
FIG. 4 is a cross-sectional schematic illustration of the preferred embodiment of FIG. 3.

With reference now to the exploded view of FIG. 3 and the cross-sectional view of FIG. 4 there is shown the improved control valve of the present invention in its preferred embodiment. The housing 14 has a central section 15 circular in shape and with a tapered cavity 15a centrally positioned therein. The spool 12 has an outside taper similar to the inside taper of housing cavity 15a. The spool 12 being of rotatable position in the housing 15. The spool and the housing cavity are sloped at approximately 8° 8° to prevent galling upon rotation — but, yet maintaining a seal tight fit.

The overall spool 12 structure is snapped and locked into the circular groove 13 of the housing 14 cavity. When the spool is snapped into place the outer bead 13a of the spool 12 together with the groove 13 forms a fluid seal to air. The bead 13a is offset with the body undercut to provide a downward force to seat the spool and to match the 8° taper of the surface 15a of the housing.

The spool 12 has a series of equally spaced vertical grooves 19a – 19n formed in its outer periphery. In operation the fluid enters the inlet 21, contacts the outside face of the spool 12 and moves down the groove 19a to the filter 33. The fluid then moves up into the scrubber notch 25 and then to outlet 23.

Figure 6:
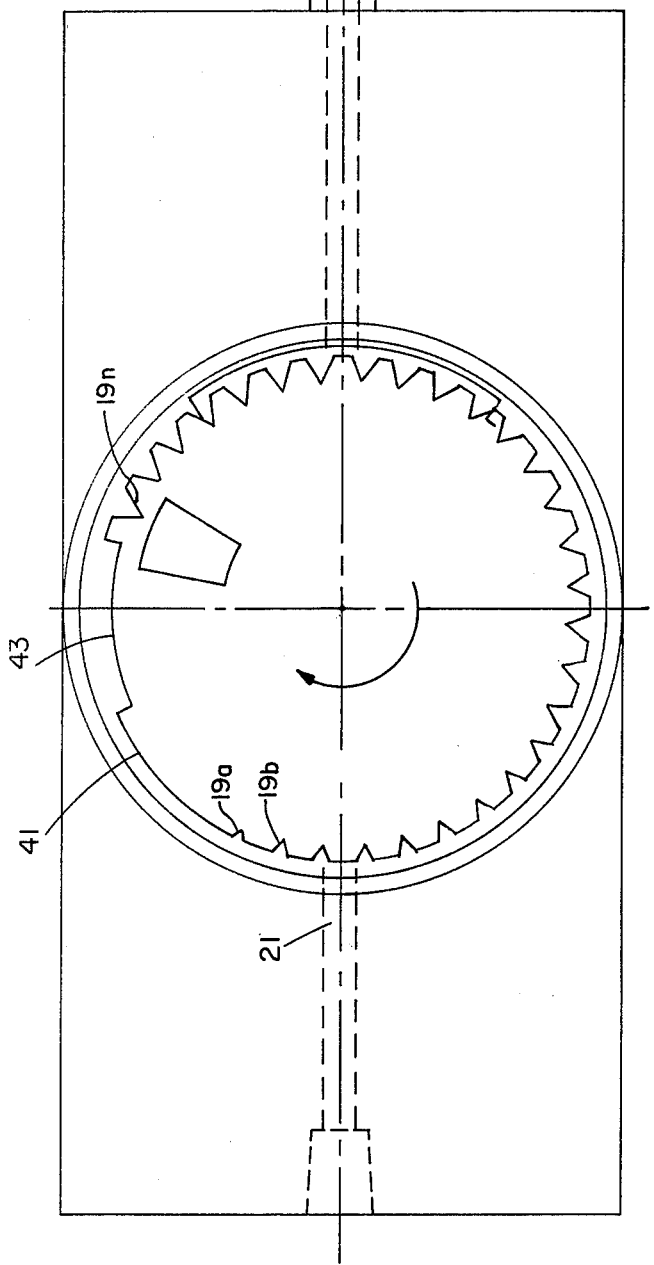
FIG. 6 is a top view schematic illustration of the groove arrangement of the control valve of the invention.

Rotation of the spool 12 presents a succession of grooves 19a through 19n to the inlet 21. Each successive groove 19a through 19n has an increased depth into the external face of the spool 12. The increased depth regulates the flow of the fluid through the valve. It is these grooves that meters the fluid passing from the inlet 21 to the outlet 23. The size, shape, length, and depth of the grooves 19a – 19n co-act with the inlet port geometry to control the amount of fluid passage and together with their spacing forms the fluid flow program. With reference to FIG. 6 the preferred embodiment is comprised of V-shaped grooves 19a – 19n with a 10° spacing interval. A solid land 41 seals the port 21 in the "off" position and a wide groove 43 provides "full flow".

The spacing between the V-shaped groove was made to have a width equal to the opening of the inlet tube at a 10° included angle as shown in FIG. 6.

With reference again to FIG. 4 the base of the housing 14 has a recessed area 33 that has a configuration together with the non-recessed area adapted to receive a washer type structure with an eccentric lobe that extends into the scrubber area 25. The eccentric shape prevents rotation of the filter 33 due to spool 12 rotation. In the recessed area 33 is positioned the filter 33 in the path of fluid flow.

The filter 33 per se comprises a cast structure of crystalline material that is commercially available. In the preferred embodiment the filter is in the order of 0.45 micron. In operation the fluid passes from the metering grooves through the filter 31 and through to the scrubber 25. In practice it is found that this filter is extremely effective in eliminating particulate matter and is effective additionally in removing many types of germs.

Adjacent the central portion of the housing 14 are the two elongated curved securing splines. As shown in FIG. 2 the 27 and 27A facilitate the securing of the control valve to the arm of the patient.

The inlet 21 is of a standard female medical luer taper that adapts with standard IV sets. The outlet 23 is a male extension that permits sealing and securing of the tube extension with a male luer needle adaptor fitting at the other end.

In the tapered portion of the inside wall of the housing 14 is a 60° wide notch type scrubber 25. The scrubber 25 collects and directs to the outlet 23 all fluid and air during the initial bleeding process achieved by rotating the spool.

Figure 5:
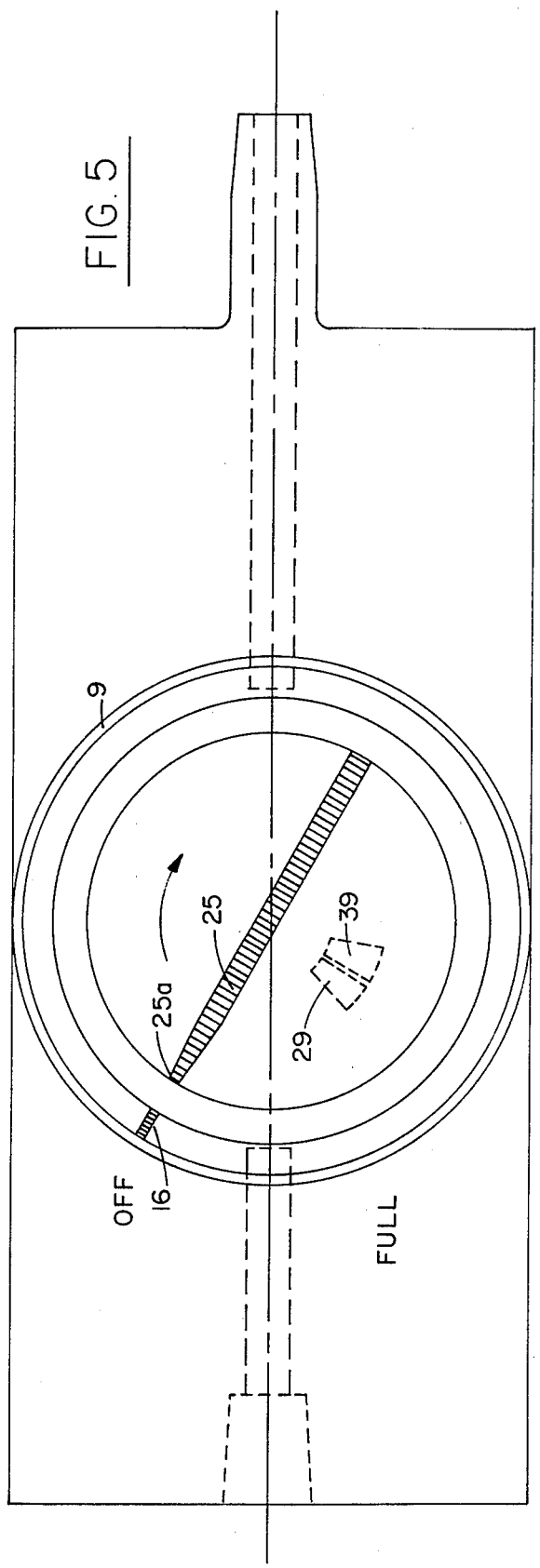
FIG. 5 is a top view partly in schematic of the preferred embodiment of FIGS. 3, and 4.

With reference to the top view of FIG. 5 and the schematic of FIG. 6 the face of the valve is shown. The spool 12 (FIG. 3) includes a pointer 25a with the turning bar 25. The clear cap 17 (FIG. 4) secures the spool 15a. The valve cannot be operated without removing the cap. The spool index 16 used in the preferred embodiment to provide a reference of spool position by matching with a pen or pencil mark on surface 9 once the prescribed flow is measured on the drip chamber. The spool 12 is recessed in its central area except for the turning bar 25.

The spool 12 includes a stop lug 29 that meets with stop lug 39 on the housing. In one contact position the openings for the passage of fluid are "full" and in the other contact position the openings are "off" the intermediate positions permit the graduated flow program of FIG. 7.

Figure 7:
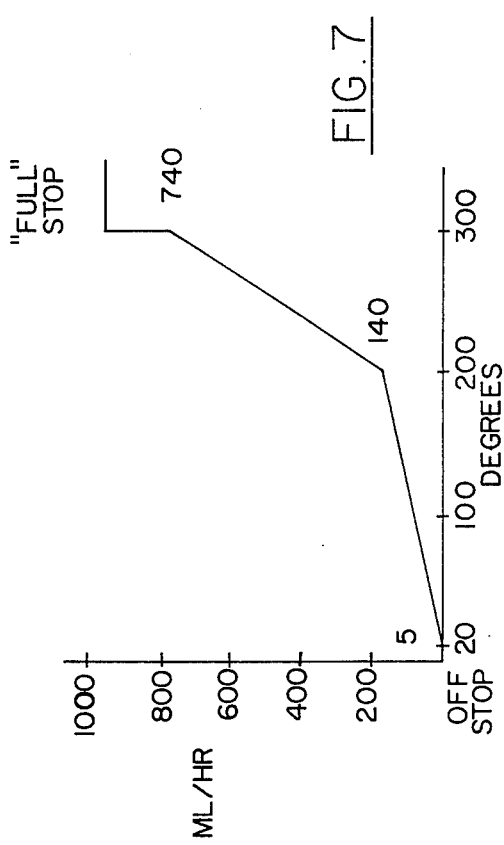
FIG. 7 is a graphical illustration typical intravenous flow program.

In operation the groove configuration and spacing as shown in FIG. 6 resulted in the flow curve of FIG. 7. This flow curve is adaptable to both the standard IV sets and may be adaptable to the so-called mini-sets. Spools with different groove configurations 12a – 12n may be substituted for the above spool to provide flow curves matched to the requirements of anesthesiology, patency and other medical applications requiring precise control at low fluid flow.

Although only a certain and specific embodiment of the invention has been shown and described, it is understood that modifications may be had thereto without departing from the true spirit and scope of the invention.

What is claimed is:

1. A control valve for regulating the gravitational liquid flow to a patient from a suspended bottle and a length of tubing; the improvement comprising:
    a spool,
    a housing having an inside diameter adapted to receive in fluid contact said spool;
    the outside wall of said spool and the inside wall of said housing having co-acting tapered surfaces to provide a fluid seal,
    said spool wall having a resilient bead projecting from its upper region and said housing having an indentation in its upper region adjacent said bead whereby when said spool is forced into position within said housing indentation, said spool provides a rotatable fluid to air seal and retainer therebetween;
    said spool having formed in its outside wall a series of grooves, means to rotate said spool in said housing,
    said housing having included an inlet port whereby said grooves in said spool when open to said inlet port controls the fluid flow through said control valve, and an outlet port,
    an adaptor connecting said tubing to said inlet port and an adaptor connecting said outlet port to entry means to the body of the patient; and
    a filter positioned between said spool and said housing outlet port for filtering said liquid.

2. The control valve of claim 1 wherein said grooves in said outside wall of said spool have a fixed spacing equal to the inlet port diameter.

3. The control valve of claim 1 wherein said grooves in said outside wall of said spool are of a predetermined size, shape, length, and depth to control the fluid passage.

4. The control valve of claim 1 wherein said housing and said spool further including engaging limit stops and wherein said engaging occurs in either limit.

5. The control valve of claim 1 wherein said housing includes a recess in its base and wherein said filter is of a shape to fit in said recess with a fluid tight fit.

6. The control valve of claim 5 wherein said recess in said housing includes a central non-recessed area adapted to receive said filter having a complimentary washer-like eccentric shape.

7. The control valve of claim 5 wherein said filter is of crystalline material.

8. The control valve of claim 1 wherein said top portion of said spool is recessed into said housing, and further including a cap positioned within said housing over said spool.

9. The control valve of claim 1 wherein said inlet adaptor is a tapered female luer fitting.

10. The control valve of claim 1 wherein said outlet adaptor is a sealed tubing with luer male adaptor.

11. The control valve of claim 1 wherein said housing has an upper surface adapted for placing an indicia thereon.

12. The control valve of claim 11 wherein said means to rotate said spool includes a pointer bar for visual reference to said indicia.

13. The control valve of claim 11 wherein said inlet port is operative to trap line air in its initial purge.

* * * * *